United States Patent
Chu et al.

(10) Patent No.: US 9,480,487 B2
(45) Date of Patent: Nov. 1, 2016

(54) LATERAL LIGHT-EMITTING DEVICE FOR CONNECTING AN INTRA-MEDULLARY GUIDE WIRE

(71) Applicant: NATIONAL YANG-MING UNIVERSITY, Taipei (TW)

(72) Inventors: Woei-Chyn Chu, Taipei (TW); Yin-Jiun Tseng, Taipei (TW); William Chu, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 632 days.

(21) Appl. No.: 13/672,343

(22) Filed: Nov. 8, 2012

(65) Prior Publication Data

US 2014/0128869 A1 May 8, 2014

(51) Int. Cl.
*A61B 17/90* (2006.01)
*A61B 17/17* (2006.01)

(52) U.S. Cl.
CPC ................ *A61B 17/1725* (2013.01)

(58) Field of Classification Search
CPC .... A61B 1/06; A61B 1/0607; A61B 1/0615; A61B 1/0623; A61B 1/063; A61B 1/0661; A61B 1/0676; A61B 1/0674; A61B 1/00032; A61B 1/041; A61B 1/00177; A61B 1/00183; A61B 19/52; A61B 19/5202; A61B 17/1725; A61N 5/0603; F21L 4/005
See application file for complete search history.

(56) References Cited

U.S. PATENT DOCUMENTS

| | | | |
|---|---|---|---|
| 5,540,691 A | | 7/1996 | Elstrom et al. |
| 5,644,438 A | * | 7/1997 | Pottash .............. A61B 1/0615 359/367 |
| 2004/0249247 A1 | * | 12/2004 | Iddan .................. A61B 1/0005 600/170 |
| 2006/0242884 A1 | * | 11/2006 | Talieh ................ A61B 1/0676 43/17.5 |
| 2007/0270864 A1 | | 11/2007 | Gurtowski |
| 2011/0054484 A1 | * | 3/2011 | Brandon ........... A61B 17/3421 606/96 |
| 2011/0257488 A1 | * | 10/2011 | Koyama ........... A61B 1/00147 600/249 |

FOREIGN PATENT DOCUMENTS

WO  WO 2009/131999 A2  10/2009
WO  WO 2009131999 A2 * 10/2009 ......... A61B 17/7011

* cited by examiner

*Primary Examiner* — Lynnsy Summitt
(74) *Attorney, Agent, or Firm* — Muncy, Geissler, Olds & Lowe, P.C.

(57) ABSTRACT

A lateral light-emitting device for connecting a medullary guide wire is disclosed. The device comprises a closed main body, a front-end protecting unit for protecting the front end of the main body, and a connecting unit disposed at the distal end of the main body. The inside of the main body is further arranged with a lighting unit, a power supply unit, a light-scattering unit, a light intensity modulating unit, if necessary, and at least one transparent window. The device is able to fit to different types of medullary guide wires. The power supply unit provides power to the lighting unit to produce light emitted to the light-scattering unit and being diverted laterally through the transparent window of the main body after suitably modulating the light intensity. Thereby, the device is illuminated from within the bone cavity to allow observing the operating screw hole location from outside of the body and to enable precisely nailing while proceeding with the intra-medullary nailing procedure.

18 Claims, 3 Drawing Sheets

LATERAL LIGHT-EMITTING DEVICE FOR CONNECTING AN INTRA-MEDULLARY GUIDE WIRE

BACKGROUND

1. Field

This disclosure relates generally to an intra-medullary guide wire and more particularly to a lateral light-emitting device capable of connecting an intra-medullary guide wire.

2. Description of Related Art

Lower extremities fractures are treated by intra-medullary nailing that is a golden standard method for the recent twenty years. The insertion of the nail requires a guide wire to guide the insertion of the intra-medullary nail into the medullary cavity.

Interlocking nail provides good fixation thus better treatment efficacy over the conventional medullary nails. During operation, it must be localized the distal and proximal screw holes and then use screws to fix the nail (locking the nail). Because the nail is embedded in the medullary cavity, so a standard approach is to use the roentgenography to "see" the screw holes and completed this procedure.

Please reference to U.S. Pat. No. 5,417,688. The optical distal targeting system and method for an intra-medullary nail for detecting the location of transverse holes of an intra-medullary nail which has been inserted into a long bone and for aligning a surgical drill to the transverse holes is disclosed. An insert having a light source at its distal end emitting non-ionizing electromagnetic radiation in the visible spectrum or infrared is inserted into the intra-medullary nail, such that the light source is placed adjacent to the transverse holes. The light source may be a directional radiation output emitting the radiation in a direction perpendicular to the axis of the intra-medullary nail. The light source may alternatively be an isotropic radiation output emitting radiation in all directions. The surgeon detects the transmitted radiation on the surface of the body of the patient and aligns the drill with the emitted radiation.

Please also reference to TW issued U.S. Pat. No. 485,036. A medullary guide wire with a self-attached lighting device is disclosed. The front end of the guide wire is self-attached with a lighting device, and the visible light or near infrared light from the lighting device will penetrate out of the tissues and bone surface and is used for detecting the screw hole. During screw hole detection, the light-emitting medullary guide wire is stayed in the nail inserted into the marrow cavity and the light emitted through the screw hole and the bone surface is observed from outside of the body. The light-emitting guide wire enables a quick and convenient way to position the screw holes while performing the intra-medullary nailing procedure.

The two structures of the above mentioned prior arts are used by illuminating from within the body to proceed the operation so as to reduce the risk of additional traumas and improve the efficacy of operations, but because the light source is arranged at the front end of the guide wire so a significant portion of the emitted light will travel axially and is not useful for detecting the screw hole which lies on the lateral side of the nail. It may thus require to increase the light power that caused higher power consumption or even injuries resulting from high temperature generated from the high light intensity.

The structure disclosed in a U.S. Pat. No. 5,417,688 has a hole dug laterally so as to divert the light to emit through lateral sides. However, because the light source is disposed in an open structure, the lighting device is easily permeated by the body fluids to cause the device malfunction or contaminate the surrounding tissues.

In addition, the lighting device and the medullary guide wire are fixed in one piece, this increases the manufacturing difficulty as the diameter of the guide wire is only about 3 mm. Furthermore, because the lighting device is arranged at the front end of the medullary guide wire, the medullary guide wire needs to be inserted into the marrow cavity, and the light source has no protecting device to protect it while proceeding the operation, it is easily to damage the light source in the marrow cavity resulting from colliding bone tissue. When this happened, the assembly of the lighting device and the medullary guide wire must be discarded all together. It will be a waste of resources.

SUMMARY

The light emitted from the lighting device inserted into the medullary cavity for positioning the screw hole is an effective method in intra-medullary nailing procedures. In order to solve the above mentioned problems and improve the luminous efficiency of the lighting device, a lateral-emitting lighting device capable of working with any kind of intra-medullary guide wire is disclosed.

To achieve the above objective, a lateral-emitting device for connecting a intra-medullary guide wire is disclosed. The device has a stand-alone closed space so that the liquid (e.g. body fluid) is unable to permeate into the device.

Another objective of this invention is to provide a protecting mechanism to the light emitting device. A protecting unit is disposed at the front end of the device for protecting the main body from colliding with the bone tissues resulting in damaging the inner structure and function of the main body.

One another objective of this invention is to provide a lateral-emitting device for connecting an intra-medullary guide wire. The individual main body with a connecting unit is capable of making the lateral-emitting device tightly connected to any kind of intra-medullary guide wire.

One another objective of this invention is to provide a lateral-emitting device for connecting an intra-medullary guide wire. A light-scattering unit is disposed inside the main body so that the light is scattered, brightness enhanced, and laterally emitted to a closed window when the emitted light hit and reflected from the curved surface of the light-scattering unit.

One another objective of this invention is to provide a lateral-emitting device for connecting an intra-medullary guide wire. A light intensity modulating unit is arranged inside the main body to modulate the light intensity to reduce the smear of the scattered light effect.

One another objective of this invention is to provide a lateral-emitting device for connecting an intra-medullary guide wire with a closed main body for preventing the body fluid from permeating in the body to cause contamination and damages. Furthermore, it makes the modulated light passed through the light intensity modulating unit and then laterally emitted through the light-scattering unit to assist fixation of the screw hole.

The lateral light-emitting device for connecting an intra-medullary guide wire, comprising: a main body, having a closed accommodating space thereinside; a front-end protecting unit, disposed in a front end of the main body; a light-scattering unit, disposed in the accommodating space and arranged in back of the front-end protecting unit; a lighting unit, disposed at a predetermined position in the accommodating space of the main body and corresponding to the light-scattering unit so as to make a light generated by the lighting unit be capable of projecting to the light-scattering unit, passing therethrough, and generating scattering; a power supply unit, arranged at the one end of the accommodating space of the main body to provide power to make the lighting unit illuminate; at least one transparent window, disposed at the side of the main body so as to make the scattered light in the accommodating space emit outwardly through the transparent window; and a connecting unit, disposed at the distal end of the main body for connecting the lateral light-emitting device and the medullary guide wire.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Any feature or structure can be removed or omitted. Throughout the drawings, reference numbers may be reused to indicate correspondence between reference elements.

DETAILED DESCRIPTION OF PREFERRED EMBODIMENTS

Although certain preferred embodiments and examples are disclosed herein, inventive subject matter extends beyond the examples in the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures; systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
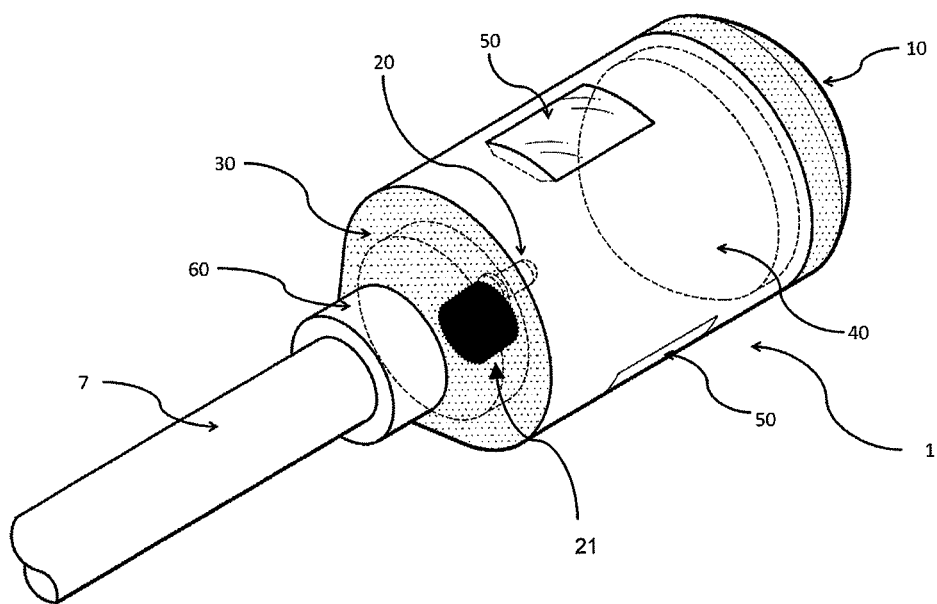
FIG. 1 is a structural drawing of a lateral light-emitting device for connecting an intra-medullary guide wire in accordance with the invention.
Figure 2:
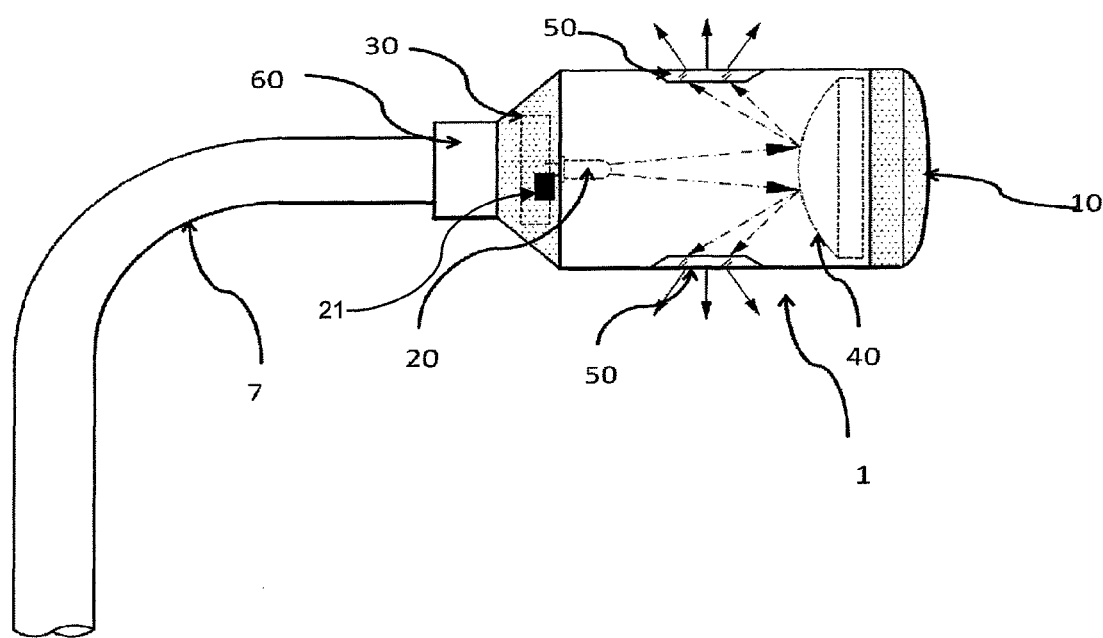
FIG. 2 is showing a preferable embodiment of the lateral light-emitting device for connecting an intra-medullary guide wire in accordance with the invention.

Please refer to FIGS. 1 and 2, which FIG. 1 is a structural drawing of a lateral light-emitting device for connecting an intra-medullary guide wire in accordance with the invention, and FIG. 2 is showing a preferable embodiment of the lateral light-emitting device for connecting an intra-medullary guide wire in accordance with the invention.

Please reference to FIG. 1, the lateral light-emitting device for connecting an intra-medullary guide wire comprises a main body 1. The main body 1 is designed as a close accommodating space to prevent the liquid (e.g. body fluid) from permeating into the body. The outside of the main body 1 is made of transparent, thermal isolation, and bio-compatibility material.

A front-end protecting unit 10 is arranged at the front end of the main body 1 used for preventing the main body 1 from colliding the bone tissues to cause damages while operating treatments. In one embodiment of this invention, the front-end protecting unit 10 is made of a hard material to protect the main body 1 to be capable of being pushed ahead smoothly. Furthermore, the front-end protecting unit 10 may be a hard material with elastic protection function. The front-end protecting unit 10 may be connected the front end of the main body 1 with any kinds of ways, or the front-end protecting unit 10 and the main body 1 are one piece.

A connecting unit 60 is arranged at the distal end of the main body 1 for connecting the intra-medullary guide wire 7. In one embodiment of this invention, the connecting unit 60 is made of an elastic and invaginated material to tightly connecting the main body 1 and the intra-medullary guide wire 7 and released them by outwardly forcing the intra-medullary guide wire 7. In addition, the connecting unit 60 has an outer metal ring (not shown) having set threads or at least one screw for fixing to tighten the outer metal ring (not shown) while fixing the connecting unit 60 and connecting the medullary guide wire 7.

The main body 1 has a light-scattering unit 40 arranged inside the close accommodating space of the main body 1 and including a reflecting surface with a convex arc shape. In one embodiment of this invention, the surface of the light-scattering unit 40 is a glass, plastic sheet, or acrylic sheet plating a metal oxide film capable of reflecting light. In another embodiment of this invention, the reflecting surface of the light-scattering unit 40 has an inclined angle capable of making the straight light be scattered to the transparent window.

A lighting unit 20 is arranged inside the close accommodating space of the main body 1 and corresponding to a predetermined position of the light-scattering unit 40. A power supply unit 30 is arranged at one end of the close accommodating space of the main body 1. The power supply unit 30 may be a micro cell power supply system to provide power to the lighting unit 20. A light intensity modulating unit 21 may be arranged between the lighting unit 20 and the power supply unit 30. The light intensity modulating unit 21 has a variable resistor to adjust the magnitude of current flowed into the lighting unit 20. In one embodiment of this invention, a straight light with suitable light intensity is emitted and forward to the light-scattering unit 40 after the power supply unit 30 is powered on to provide power to the lighting unit 20 and then the light intensity of the lighting unit 20 is modulated by the light intensity modulating unit 21.

At least one transparent window 50 is selected from one of following materials for easily making the light pass through: glass, acrylic, and plastic to become a sealed transparent block and arranged at side of the main body 1. The light is emitted outside through the transparent window 50 while the light emitted from the lighting unit 20 arranged in the close accommodating space is scattered by the light-scattering unit 40.

In addition, the surface of the transparent window 50 may be arranged a reflect mirror with prism angles. Accordingly, the light is emitted outwardly after being enhanced and focused.

Please reference to FIG. 2, which is showing the laterally emitting process of the lateral-emitting device for connecting the intra-medullary guide wire. In one embodiment of this invention, the light source of the lighting unit 20 is LED and the power supply unit 30 is battery used for providing power to the lighting device 20. After light intensity of the lighting unit 20 is modulated by the light intensity modulating unit 21, the light is straightly emitted. When the straight light is contacting the light-scattering unit 40, it may be scattered by the arc convex reflecting surface (mirror) of the light-scattering unit 40. The scattered light is emitted to the transparent window 50 with prism angels and modulated and focused through the transparent window 50 to make the focused light emitted from the transparent window 50 laterally.

For the above mentioned, the lateral-emitting device of this invention may change the light emitting direction, and control the laterally emitted light to be focused and emitted the clear light to be easily positioned and observed out of the body.

Figure 3:
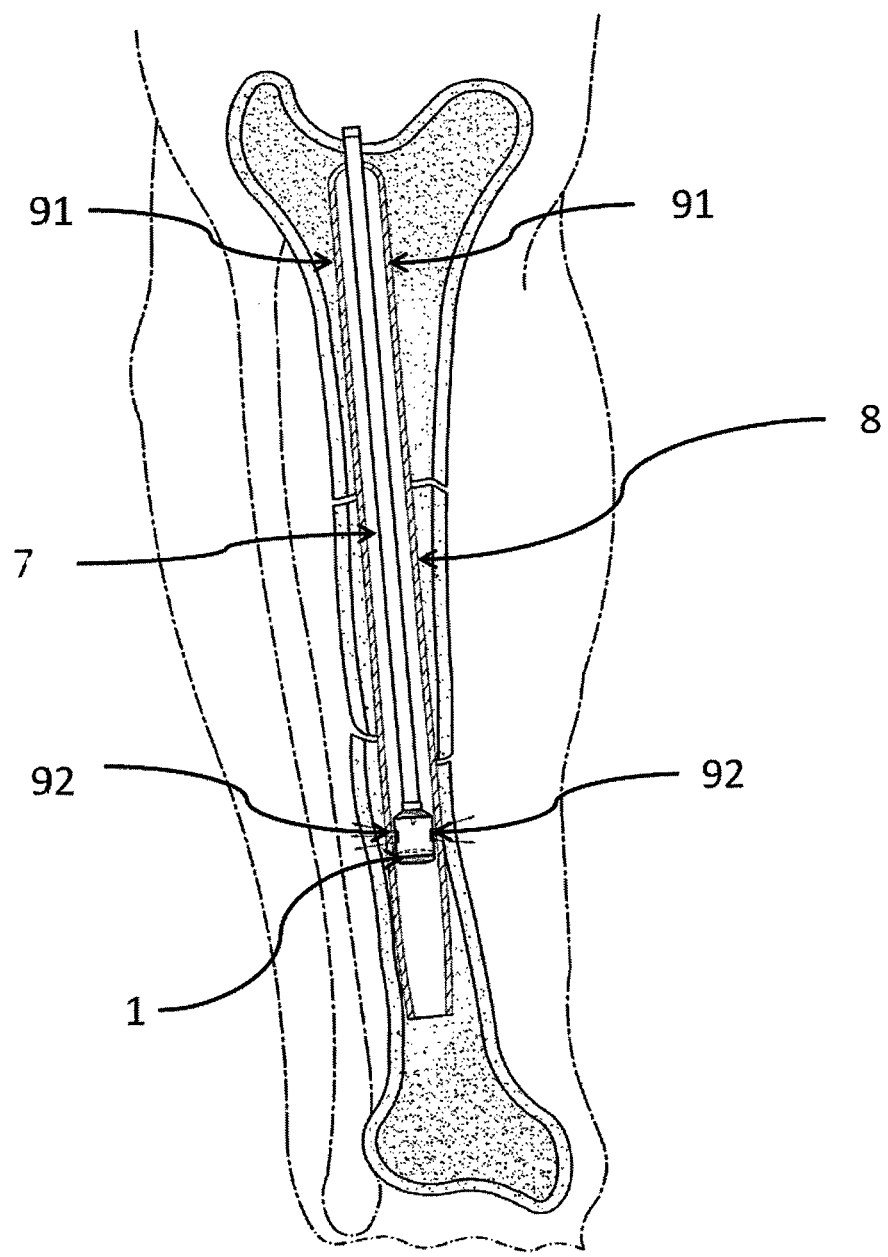
FIG. 3 is a showing the fixed type intra-medullary nailing used in the tibial fractures by the lateral light-emitting device for connecting an intra-medullary guide wire in accordance with the invention.

Please reference to FIG. 3, which is showing the fixed type intra-medullary nailing used in the tibial fractures by the lateral light-emitting device for connecting an intra-medullary guide wire in accordance with the invention. The detail steps are:

(1). The lateral-emitting device is connected to one end of a flexible intra-medullary guide wire 7 by the connecting unit 60. The connecting unit 60 has a socket head so as to connect the medullary guide wire 7 tightly by toothed structure with a frictional force therebetween.

(2). When positioning the hole of the nail, it is started from the farther two distal ends 91. The intra-medullary guide wire 7 is retracted backwardly to make the lateral-emitting device 10 be positioned at the distal end 91 of the nail (evaluated by the length of the nail). The power supply unit 30 is to provide the power to the lighting unit 20 of the lateral-emitting device 10. After the light intensity from the lighting unit 20 is modulated by the light intensity modulating unit 21, the lighting unit 20 is emitted the straight light with suitable intensity. The light is scattered after the emitted straight light hits the light-scattering unit 40. The scattered light is laterally emitted through the transparent window 50. Next, the intra-medullary guide wire 7 connected to the lateral-emitting device 10 is moved back and forth till the light goes through from the desired positioning hole. Continue the movement based on the above steps and simultaneously observe the light coming out of the screw hole. If the light intensity is gradually enhanced, continue moving in the same direction. If not, move in the opposite direction until the rough location of the desirable positioned hole is determined. The light source of the lighting unit 20 is moved back and forth gradually near the determined rough location till the location of the brightest point is capable of being determined. And further change the observing angle till a symmetrical complete circle bright point is observed. The center of the circle is a center of the screw hole of the nail. Mark the location of the center point.

(3). The intra-medullary guide wire 7 is retracted backwardly later to make the light source of the lateral-emitting device 10 move away from the marked center at previous step. The skin with the marked center is incised own to the bone, the bone is drilled by a drill, and then the fixed screw is locked therein.

(4). Repeat steps (2) and (3) to the rest distal screw holes 91 and proximal screw holes 92, and lock into the fixed screw.

After above mentioned steps, the lighting effect is good to make the holes of the nail clear while the intra-medullary connecting the lateral-emitting device is used for fixed type intra-medullary nailing. The light source may not be damaged or broken during the process and the body fluid may not be permeated after operating with the lateral-emitting device.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Thus, it is intended that the scope of the inventions herein disclosed should not be limited by the particular embodiments described above, but should be determined only by a fair reading of the claims that follow.

The following is claimed:

1. A lateral light-emitting device for connecting an intra-medullary guide wire, comprising:
a main body, having a close accommodating space thereinside;
a front-end protecting unit, disposed in a front end of the main body;
a light-scattering unit, disposed in the accommodating space and arranged in back of the front-end protecting unit;
a lighting unit, disposed at a predetermined position in the accommodating space of the main body and corresponding to the light-scattering unit so as to make a light generated by the lighting unit be capable of projecting to the light-scattering unit, passing therethrough, and generating scattering;
a power supply unit, arranged at one end of the accommodating space of the main body to provide power to make the lighting unit illuminate;
at least one transparent window, disposed at a side of the main body so as to make scattered light in the accommodating space emit outwardly through the transparent window; and
a connecting unit, disposed at a distal end of the main body for connecting the lateral light-emitting device and the intra medullary guide wire;
wherein a surface of the transparent window has a reverse cone shape with a light-reflecting surface so as to make the light emit outwardly.

2. The device of claim 1, wherein the main body is made of transparent, thermal isolation, and bio-compatibility material.

3. The device of claim 1, wherein the front-end protecting unit is made of a hard material to protect the main body to be capable of being pushed ahead smoothly.

4. The device of claim 1, wherein the transparent window is selected from one of following materials for easily making the light pass through: glass, acrylic, and plastic.

5. The device of claim 1, wherein a surface of the light-scattering unit is a reflecting surface a convex arc shape.

6. The device of claim 5, wherein the surface of the light-scattering unit is a glass, a plastic sheet, or an acrylic sheet plating a metal oxide film.

7. The device of claim 5, wherein the reflecting surface of the light-scattering unit has an inclined angle capable of making a straight light be scattered to the transparent window.

8. The device of claim 1, wherein the power supply unit is a micro cell that provides power to the lighting unit.

9. The device of claim 1, further comprises a light intensity modulating unit arranged between the lighting unit and the power supply unit so as to modulate light intensity of the lighting unit.

10. The device of claim 9, wherein the light intensity modulating unit has a variable resistor to adjust a magnitude of current flowed into the lighting unit.

11. The device of claim 1, wherein the connecting unit has a socket head so as to connect the medullary guide wire tightly by a frictional force therebetween.

12. A lateral light-emitting device for connecting an intra-medullary guide wire, comprising:
- a main body, having a close accommodating space there-inside;
- a front-end protecting unit, disposed in a front end of the main body;
- a light-scattering unit, disposed in the accommodating space and arranged in back of the front-end protecting unit;
- a lighting unit, disposed at a predetermined position in the accommodating space of the main body and corresponding to the light-scattering unit so as to make a light generated by the lighting unit be capable of projecting to the light-scattering unit, passing therethrough, and generating scattering;
- a power supply unit, arranged at one end of the accommodating space of the main body to provide power to make the lighting unit illuminate;
- at least one transparent window, disposed at a side of the main body so as to make scattered light in the accommodating space emit outwardly through the transparent window;
- a connecting unit, disposed at a distal end of the main body for connecting the lateral light-emitting device and intra the medullary guide wire;
- wherein the connecting unit has a socket head so as to connect the intra medullary guide wire tightly by a frictional force therebetween.

13. The device of claim 12, wherein a surface of the light-scattering unit is a reflecting surface with a convex arc shape.

14. The device of claim 13, wherein the surface of the light-scattering unit is a glass, a plastic sheet, or an acrylic sheet plating a metal oxide film.

15. The device of claim 13, wherein the reflecting surface of the light-scattering unit has an inclined angle capable of making a straight light be scattered to the transparent window.

16. The device of claim 12, wherein the power supply unit, which is micro cell that provides power to the lighting unit.

17. The device of claim 12, further comprises a light intensity modulating unit arranged between the lighting unit and the power supply unit so as to modulate light intensity of the lighting unit.

18. The device of claim 17, wherein the light intensity modulating unit has a variable resistor to adjust a magnitude of current flowed into the lighting unit.

* * * * *